(12) United States Patent
Kubo et al.

(10) Patent No.: US 6,837,925 B2
(45) Date of Patent: Jan. 4, 2005

(54) COLORING PEARLESCENT FLAKE PIGMENT, MANUFACTURING METHOD OF THE SAME AND COSMETIC PRODUCT CONTAINING THE SAME

(75) Inventors: Yasushi Kubo, 1-16, Nunohashi 3-chome, Hamamatsu-shi, Shizuoka 432-8012 (JP); Hideji Kagawa, Osaka (JP)

(73) Assignees: Yasushi Kubo, Hamamatsu (JP); Daito Kasei Kogyo Co., Ltd., Osaka (JP)

( * ) Notice: Subject to any disclaimer, the term of this patent is extended or adjusted under 35 U.S.C. 154(b) by 0 days.

(21) Appl. No.: 10/447,276

(22) Filed: May 29, 2003

(65) Prior Publication Data

US 2004/0237843 A1 Dec. 2, 2004

(51) Int. Cl.$^7$ ............................................... C04B 14/00

(52) U.S. Cl. ..................... 106/486; 106/415; 106/416; 106/468; 106/486; 106/487; 424/69

(58) Field of Search ................................ 106/415–417, 106/486–487, 468; 424/63–64, 69

(56) References Cited

FOREIGN PATENT DOCUMENTS

JP      2001-234090      *  8/2001

* cited by examiner

Primary Examiner—C. Melissa Koslow
Assistant Examiner—Shalie A. Manlove
(74) Attorney, Agent, or Firm—Armstrong, Kratz, Quintos, Hanson & Brooks, LLP

(57) ABSTRACT

A coloring pearlescent flake pigment capable of providing pearl-like luster caused by interference color and a vivid color caused by a tar color is provided as a new material which contributes to the diversification of cosmetics and paints thanks to its powdery smoothness and the visual effect as well as covering protection effect in an application layer. The coloring pearlescent flake pigment having a double coating layer which is formed on inorganic flake-like particles and which is composed of a high-refraction-index metal oxide (e.g., titanium dioxide) and a hydrotalcite-like coloring composition is produced by the following process: In an aqueous suspension containing inorganic flake-like particles coated with a high-refraction-index metal oxide, a soluble anionic dye, a plurality of soluble metallic salts which are the raw materials of a double hydroxide, and a neutralizing base including urea are allowed to react, so that a hydrotalcite-like coloring composition precipitates on the inorganic flake-like particles.

6 Claims, No Drawings

COLORING PEARLESCENT FLAKE PIGMENT, MANUFACTURING METHOD OF THE SAME AND COSMETIC PRODUCT CONTAINING THE SAME

TECHNICAL FIELD

The present invention relates to coloring pearlescent flake pigments, their manufacturing method and cosmetic products containing such pigments, the pigments being useful because they have powdery smoothness and give a visual effect as well as a covering protection effect when forming an application layer and having wide applications as a colorant in the field of make-up products which require safety to human bodies.

BACKGROUND ART

Mica-based coloring pearlescent pigments of golden, dark-blue and carminic colors have been developed and widely used in the fields of special painting and make-up products, in which in order to overlay a color caused by selective absorption on an interference color caused by a colorless metal oxide coating layer having high refraction index such as titanium oxide and zirconium oxide, an inorganic coloring ingredient (e.g., iron oxide) is added to the coating layer, or alternatively, an inorganic or organic colorant is applied to the particle surfaces.

Conventional coloring by use of an inorganic coloring ingredient, however, presents the disadvantage of limited hues and low color saturation. In coloring with an organic pigment, applicable dyes are limited in view of the effects on human bodies and dissolution resistance. The present invention aims to provide coloring pearlescent flake pigments, their manufacturing method and cosmetic products containing such pigments, which pigments provide red, yellow and blue colors with high saturation, using anionic tar colors approved for use in foods, medical products, quasi drags and cosmetics by the Food Sanitation Law and the Medicine Act.

DISCLOSURE OF THE INVENTION

The present inventors have found a method in which an anionic tar color is introduced and insolubilized between the layers of a hydrotalcite-like inorganic layered double hydroxide to form a coloring composition (hereinafter referred to as "hydrotalcite-like coloring composition") as a uniform coating layer on the surfaces of inorganic flake-like particles such as talc, mica, sericite or kaolin, and developed a novel coloring flake pigment (Japanese Patent Publication KOKAI Gazette No. 2001-234090). They applied this method to pearlescent inorganic flake particles, thereby making the present invention.

Specifically, the invention provides a coloring pearlescent flake pigment characterized by a coating layer of a hydrotalcite-like coloring composition formed on the surfaces of pearlescent inorganic flake-like particles.

A method of manufacturing the coloring pearlescent flake pigment is characterized in that a soluble anionic dye, a plurality of soluble metallic salts and a neutralizing base are allowed to react within an aqueous suspension containing pearlescent inorganic flake-like particles such that a hydrotalcite-like coloring composition is precipitated on the surfaces of the pearlescent inorganic flake-like particles.

The invention further provides a cosmetic product containing the above coloring pearlescent flake pigment.

The hydrotalcite-like coloring composition is a coloring composition having a lamellar crystal structure obtained by introducing a dye anion as an interlayer anion ($A^{n-}$) into a hydrotalcite-like layered double hydroxide $[M_{1-x}M'_x(OH)_2]$ $(A^{n-})_{x/n} mH_2O (0.2 \leq x \leq 0.33)$ constituted by a bivalent metal ion (M) such as magnesium, calcium and zinc and a tervalent metal ion (M) such as aluminum. The methods of producing this coloring composition are roughly classified into three types. The first method is the ion exchange process in which anion exchange is carried out by bringing Cl-type hydrotalcite containing $Cl^-$ as $A^{n-}$ into contact with an anionic dye aqueous solution. The second method is the restructuring process in which $CO_3$-type hydrotalcite is baked at about 500° C., dehydrated and decarbonized thereby once producing an amorphous oxide which is in turn allowed to react to a dye anion within an aqueous solution, so that an anion-exchanged, hydrotalcite structure is reproduced. The third method is the direct generation process in which dye-anion-type hydrotalcite is precipitated by mixing, through an appropriate process, a plurality of metallic salt solutions which satisfy the above composition formula, a dye solution and a basic solution in an amount equal to its neutralization equivalent. The following is the percentages of coloring matters contained in the coloring compositions attained by the above methods with respect to the theoretical amount derived from (the above composition formula. In the case of the red food color FD&C Red #6, the first and second methods produce hydrotalcite-like coloring compositions having dye anion contents of 75% and 45%, respectively, whereas the third method produces a hydrotalcite-like coloring composition having a dye anion content of 95% or more (Kubo, Tsuji, Bulletin issued by "Japan Society of Color Material" 69[10], pp667–677 (1996)). Although any of the above methods may be employed in the invention, the direct generation process is the most suitable for producing thick-color coloring flake pigments.

Regarding metallic salts used in the manufacturing method of the invention, chlorides, sulfates and nitrates etc. of magnesium, calcium and zinc etc. are used as the bivalent metals, while chlorides, sulfates, nitrates etc. of aluminum and sodium aluminate are used as the tervalent metals. Although sodium hydroxide, ammonia, urea etc. are used as the neutralizing base, sodium carbonate cannot be used because it preferentially produces the $CO_3$ type hydrotalcite. As the anionic dye, soluble anionic dyes selected from tar colors for use in food, medical products, quasi drugs and cosmetics approved by the Food Sanitation Law and the Medicine Act are used. Examples of the anionic dye include the yellow food color FD&C Yellow #5 (Tartrazine), yellow food color FD&C Yellow #6 (Sunset Yellow FCF), blue food color FD&C Blue #1 (Brilliant Blue FCF), red food color FD&C Red #3 (Erythrosine), red food color FD&C Red #28 (Floxine B) and red food color FD&C Red #6 (Lithol Rubin B).

In the manufacturing method, the above raw materials are respectively dissolved in water (the materials having less solubility such as the red food color FD&C Red #6 are suspended in water), thereby preparing two, four or five (in cases where urea is used) kinds of individual solutions depending on the type of the anionic dye used. In the final stage, these solutions are mixed together with the suspension containing pearlescent inorganic flake-like particles dispersed therein. The flake particle suspension and the raw material solutions which can be mixed with the dye solution beforehand are first put in a reaction vessel. The other raw material solutions are mixed dropwise with the above solutions with vigorous stirring. Combinations of the raw material solutions which can be mixed beforehand are determined taking the reactivity of each material into account.

When using a dye lacking acid resistance and base resistance such as the blue food color FD&C Blue #1, it is necessary to drop a metallic salt solution and a neutralizing base solution simultaneously with dropping of the dye solution in order to constantly keep the pH of the dye solution within the neutral zone in the reaction vessel. Dyes having high base resistance such as the red food color FD&C Red #6 can be mixed with a sodium aluminate solution or neutralizing base solution beforehand. By warming and aging at 80° C. or more after completion of the dropwise mixing, a hydrotalcite-like coloring composition is gradually generated on the surfaces of the pearlescent inorganic flake-like particles. The generating speed depends on the raw materials as well as the mixing method and ranges from half a day to a couple of days.

Although the surfaces of the pearlescent inorganic flake-like particles can be coated with a hydrotalcite-like coloring composition by the method described earlier, the characters of the resulting coated material considerably varies depending on the raw materials and neutralizing method employed. Where a metal chloride is used as the raw material and neutralization is carried out with sodium hydroxide, the particle surfaces are covered with a fine particle aggregate, so that the smoothness of the particle surfaces is lost. If the same raw material is used and one sixth to all the amount of sodium hydroxide is replaced with urea, uniform smooth coating will be attained.

The hydrotalcite-like coloring composition precipitates on and covers the surfaces of micaceous pearlescent inorganic flake-like particles for the following reason. The metal chloride constituting the surface layers of the pearlescent inorganic flake-like particles has a certain degree of orientation with respect to the crystal structure of the underlying clay mineral. Therefore, the hydrotalcite-like structure having conformance to the structure of the clay mineral due to the brucite $(Mg(OH)_2)$ type hexagonal-plane zona reticularis is also conformable to the metal oxide layer through the arrangement of oxygen ions. By virtue of this, generation of the hydrotalcite-like structure from the raw material mixture solution on the surfaces of the flake particles is facilitated. However, if core generations occur simultaneously at many points on the surfaces, the surfaces will be coated with a fine particle aggregate, resulting in a loss of surface smoothness. It is assumed that the replacement of part or all of the neutralizing base with urea decreases the speed of core generations and restricts random core generations so that smooth surface coating can be achieved.

The invention enables a novel coloring pearlescent flake pigment which provides pearl-like luster caused by interference color and vivid coloring by a tar color and which is a useful colorant having wide applications in cosmetics and painting requiring safety to human bodies.

BEST MODE FOR CARRYING OUT THE INVENTION

Next, there will be explained representative examples and compositions to discuss the preferred embodiments of the coloring pearlescent flake pigment of the invention, its manufacturing method and cosmetics containing such pigment. It should be noted that these examples do not limit the technical scope of the invention but are construed as illustrative only.

EXAMPLE 1

11.6 g of the red food color FD&C Red #6 (purity: 92.5%), 620 mL of 0.5N-NaOH and 50.0 g of pearl mica (produced by Nihon Koken Kogyo Co., Ltd., color: silver, grain size: 5 to 30 μm, $Tio_2$ coverage: 38%) were put in a 2 litter Erlenmeyer flask and dissolved into water which had been boiled and decarbonized, thereby preparing a uniform dispersion liquid in an amount of 1,000 mL in total. Apart from this, 13.6 g of $ZnCl_2$, and 12.1 g of $AlCl_3$ $6H_2O$ were dissolved into water to prepare 300 mL of a solution. This solution was added dropwise to the above dispersion solution at room temperature for one hour, with vigorous stirring. Water was then added to prepare 1,500 mL (total amount) of a solution and stirring was continued for another one hour at room temperature, followed by heating to 100° C. and reflux stirring for 24 hours. Through this aging process, a hydrotalcite-like coloring composition is produced on the surfaces of the pearl mica particles, causing vivid red color. After completion of the aging, the product was cooled down to room temperature, filtered, repeatedly washed with water until the filtrate became substantially transparent, and then dried at 50° C. Through this process, 73.3 g of a red-color pearlescent flake pigment was obtained. The product tended to agglutinate during drying. When observing the product with a scanning electron microscope, it was found that a fine precipitate was accumulated on the surfaces of the flake particles.

EXAMPLE 2

10.0 g of the yellow food color FD&C Yellow #5 (purity: 89.4%), 620 mL of 0.5N-NaOH, and 50.0 g of pearl mica (produced by Merck Japan Ltd., color: silver, grain size: 10 to 60 μm, $Tio_2$ coverage: 29%) were put in a 2 litter Erlenmeyer flask and dissolved into water which had been boiled and decarbonized, thereby preparing 1,000 mL (total amount) of a uniform dispersion liquid. Apart from this, 20.3 g of $MgCl_2$ $6H_2O$ and 12.1 g of $AlCl_3$ $6H_2O$ were dissolved into water to prepare 300 mL of a solution. This solution was added dropwise to the above dispersion solution at room temperature for one hour, with vigorous stirring. Thereafter, the same procedure as in Example 1 was taken, thereby obtaining 72.6 g of a yellow-color pearlescent flake pigment which exhibited characteristics similar to those of the product obtained in Example 1.

EXAMPLE 3

12.4 g of the yellow food color FD&C Yellow #6 (purity: 91.6%), 620 mL of 0.5N-NaOH, and 50.0 g of pearl mica (produced by Merck Japan Ltd., color: silver, grain size: 10 to 60 μm, $Tio_2$ coverage: 29%) were put in a 2 litter Erlenmeyer flask and dissolved into water which had been boiled and decarbonized, thereby preparing 1,000 mL (total amount) of a uniform dispersion liquid. Apart from this, 20.3 g of $MgCl_2$ $6H_2O$ and 12.1 g of $AlCl_3$ $6H_2O$ were dissolved into water to prepare 300 mL of a solution. This solution was added dropwise to the above dispersion solution at room temperature for one hour, with vigorous stirring. Thereafter, the same procedure as in Example 1 was taken, thereby obtaining 72.1 g of an orange-color pearlescent flake pigment which exhibited characteristics similar to those of the product obtained in Example 1.

EXAMPLE 4

21.6 g of the blue food color FD&C Blue #1 (purity: 91.6%), and 50.0 g of pearl mica (produced by Engelhard Corporation, color: silver, average grain size: 28 μm, $Tio_2$ coverage: 17%) were put in a 2 litter Erlenmeyer flask and dissolved into water which had been boiled and decarbonized, thereby preparing 300 mL (total amount) of a uniform dispersion liquid. Apart from this, 20.3 g of $MgCl_2$ $6H_2O$ was dissolved into water to prepare 300 mL of a solution, and 12.1 g of $AlCl_3$ $6H_2O$ was dissolved into water to prepare 300 mL of a solution. These two solutions and 300 mL of a 1N-NaOH solution were simultaneously added dropwise to the above dispersion solution at room temperature for one hour, with vigorous stirring. Subsequently, water was added to the mixture thereby obtaining 1,500 mL of a solution in total. The product was then subjected to heating to 100° C. and 24-hour reflux stirring. Through this aging process, a hydrotalcite-like coloring composition is generated on the surfaces of the pearl mica particles, causing vivid blue color. Thereafter, the same procedure as in Example 1 was taken, thereby obtaining 72.2 g of a blue-color pearlescent flake pigment which exhibited characteristics similar to those of the product obtained in Example 1.

EXAMPLE 5

11.6 g of the red food color FD&C Red #6 (purity: 92.5%), 300 mL of 0.5N-NaOH, 50.0 g of pearl mica (produced by Engelhard Corporation, average grain size: 28 μm, $Tio_2$ coverage: 17%), 20.3 g of $MgCl_2$ $6H_2O$, 12.1 g of $AlCl_3$ $6H_2O$, and 41.9 g of urea were put in a 2 litter Erlenmeyer flask to prepare 1,500 mL (total amount) of a uniform dispersion liquid. The product was then subjected to heating to 100° C. and 24-hour reflux stirring. Neutralizing reaction proceeded along with decomposition of urea, and a hydrotalcite-like coloring composition precipitated on the surfaces of the pearl mica particles, causing vivid red color. Thereafter, the same procedure as in Example 1 was taken, thereby obtaining 73.3 g of a red-color pearlescent flake pigment. This product was a powder having better smoothness than that of Example 1 because less aggregation occurred during the drying phase. When observing the product with a scanning electron microscope, it was found that the surfaces of the flake-like particles were uniformly covered with a precipitate.

EXAMPLE 6

10.0 g of the yellow food color FD&C Yellow #5 (purity: 89.4%), 50.0 g of pearl mica (produced by Engelhard Corporation, average grain size: 28 μm, $Tio_2$ coverage: 17%), 13.6 g of $ZnCl_2$, 12.1 g of $AlCl_3$ $6H_2O$, and 41.9 g of urea were put in a 2 litter Erlenmeyer flask to prepare 1,500 mL (total amount) of a uniform water dispersion. Thereafter, the same procedure as in Example 5 was taken, thereby obtaining 67.8 g of a yellow-color pearlescent flake pigment. This product was a powder having better smoothness than that of Example 2 because less aggregation occurred during the drying phase.

EXAMPLE 7

12.4 g of the yellow food color FD&C Yellow #6 (purity: 91.6%), 50.0 g of pearl mica (produced by Nihon Koken Kogyo Co., Ltd., color: silver, grain size: 5 to 30 μm, $Tio_2$ coverage: 38%), 20.3 g of $MgCl_2$ $6H_2O$, 12.1 g of $AlCl_3$ $6H_2O$, and 41.9 g of urea were put in a 2 litter Erlenmeyer flask to prepare 1,500 mL (total amount) of a uniform dispersion liquid. Thereafter, the same procedure as in Example 5 was taken, thereby obtaining 73.1 g of an orange-color pearlescent flake pigment. This product was a powder having better smoothness than that of Example 3 because less aggregation occurred during the drying phase.

EXAMPLE 8

21.6 g of the blue food color FD&C Blue #1 (purity: 91.6%), 50.0 g of pearl mica (produced by Engelhard Corporation, average grain size: 28 μm, $Tio_2$ coverage: 17%), 13.6 g of $ZnCl_2$, 12.1 g of $AlCl_3$ $6H_2O$, and 41.9 g of urea were put in a 2 litter Erlenmeyer flask to prepare 1,500 mL (total amount) of a uniform water dispersion. This water dispersion was then subjected to heating to 100° C. and 24-hour reflux stirring. Neutralizing reaction proceeded along with decomposition of urea, and a hydrotalcite-like coloring composition precipitated on the surfaces of the pearl mica particles, causing vivid blue color. Thereafter, the same procedure as in Example 5 was taken, thereby obtaining 79.2 g of a dark blue color pearlescent flake pigment. This product was a powder having better smoothness than that of Example 4 because less aggregation occurred during the drying phase.

EXAMPLE 9

5.4 g of the blue food color FD&C Blue #1 (purity: 91.6%), 50.0 g of pearl mica (produced by Engelhard Corporation, average grain size: 28 μm, $Tio_2$ coverage: 17%), 3.40 g of $ZnCl_2$, 3.03 g of $AlCl_3$ $6H_2O$, and 10.5 g of urea were put in a 2 litter Erlenmeyer flask to prepare 1,500 mL (total amount) of a uniform water dispersion. Thereafter, the same procedure as in Example 8 was taken, thereby obtaining 56.4 g of a blue-color pearlescent flake pigment having better smoothness.

EXAMPLE 10

1.35 g of the blue food color FD&C Blue #1 (purity: 91.6%), 50.0 g of pearl mica (produced by Engelhard Corporation, average grain size: 28 μm, $Tio_2$ coverage: 17%), 0.85 g of $ZnCl_2$, 0.76 g of $AlCl_3$ $6H_2O$, and 2.62 g of urea were put in a 2 litter Erlenmeyer flask to prepare 1,500 mL (total amount) of a uniform water dispersion. Thereafter, the same procedure as in Example 8 was taken, thereby obtaining 50.8 g of a pale blue color pearlescent flake pigment having better smoothness and clearer pearl-like luster.

EXAMPLE 11

By use of the coloring pearlescent flake pigment obtained in Example 5, a lip stick having the following composition was prepared.

| Oil content: | |
|---|---|
| microcrystalline wax | 10 parts |
| ceresin | 10 parts |
| toriiso-octanoate glyceryl | 10 parts |
| vaseline | 10 parts |
| toriiso-glycerate glyceryl | 20 parts |
| Powder: | |
| titanium dioxide | 2 parts |
| the pigment of the invention (Example 5) | 18 parts |

Manufacturing process: The wax and oil solutions are melted by heating and uniformly mixed. The powders are then added to and with the mixture, using a homomixer such that the particles of the powders are evenly dispersed. Thereafter, the product is poured into a die and rapidly cooled to form it into a stick-shape.

What is claimed is:

1. A coloring pearlescent flake pigment containing a hydrotalcite-like layered double hydroxide which contains a dye anion between its crystalline layers and which is formed on the surfaces of pearlescent inorganic flake-like particles as a coating layer, wherein the pearlescent inorganic flake-like particles are inorganic flake-like particles containing a natural clay mineral selected from the group consisting of talc, mica, sericite and kaolin or an artificial clay mineral, said natural or artificial mineral being coated with a metal oxide having high index of refraction.

2. The coloring pearlescent flake pigment according to claim 1, wherein said hydrotalcite-like layered double hydroxide is a double hydroxide containing aluminum and at least one bivalent metal selected from the group consisting of magnesium, calcium and zinc.

3. The coloring pearlescent flake pigment according to claim 1, wherein said dye anion is an anion derived from a soluble anionic dye selected from tar colors for foods, medical products, quasi drugs and cosmetics which tar colors are certified by the Food Sanitation Law or the Medicine Act.

4. A method for manufacturing a coloring pearlescent flake pigment containing a hydrotalcite-like layered double hydroxide which contains a dye anion between its crystalline layers and which is formed on the surfaces of pearlescent inorganic flake-like particles as a coating layer, the pearlescent inorganic flake-like particles being inorganic flake-like particles containing a natural clay mineral selected from the group consisting of talc, mica, sericite and kaolin or an artificial clay mineral, said natural or artificial mineral being coated with a metal oxide having high index of refraction, wherein a soluble anionic dye, a plurality of soluble metallic salts serving as the raw materials of the layered double hydroxide and a neutralization salt are allowed to react within an aqueous suspension containing pearlescent inorganic flake-like particles to precipitate the hydrotalcite-like layered double hydroxide on the surfaces of the pearlescent inorganic flake-like particles.

5. The method for manufacturing a coloring pearlescent flake pigment according to claim 4, wherein at least part of or all of the neutralizing base is urea.

6. A cosmetic product containing a coloring pearlescent flake pigment containing a hydrotalcite-like layered double hydroxide which contains a dye anion between its crystalline layers and which is formed on the surfaces of pearlescent inorganic flake-like particles as a coating layer, the pearlescent inorganic flake-like particles being inorganic flake-like particles containing a natural clay mineral selected from the group consisting of talc, mica sericite and kaolin or an artificial clay mineral, said natural or artificial mineral being coated with a metal oxide having high index of refraction.

* * * * *